US009417207B2

(12) United States Patent
Marra et al.

(10) Patent No.: US 9,417,207 B2
(45) Date of Patent: Aug. 16, 2016

(54) GAS SENSING APPARATUS

(75) Inventors: Johan Marra, Eindhoven (NL); Johan Hendrik Klootwijk, Eindhoven (NL); Jacobus Bernardus Giesbers, Son (NL); Nico Maris Adriaan De Wild, Eindhoven (NL); Marcel Bulder, Eindhoven (NL); Rogier Adrianus Henrica Niessen, Eindhoven (NL); Peter Van Der Linde, Amersfoort (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 183 days.

(21) Appl. No.: 14/232,323

(22) PCT Filed: Jul. 9, 2012

(86) PCT No.: PCT/IB2012/053501
§ 371 (c)(1),
(2), (4) Date: Jan. 13, 2014

(87) PCT Pub. No.: WO2013/008170
PCT Pub. Date: Jan. 17, 2013

(65) Prior Publication Data
US 2014/0174154 A1 Jun. 26, 2014

(30) Foreign Application Priority Data

Jul. 13, 2011 (EP) .................................... 11173728

(51) Int. Cl.
G01N 7/00 (2006.01)
G01N 9/00 (2006.01)
(Continued)

(52) U.S. Cl.
CPC ............ *G01N 27/403* (2013.01); *G01N 1/2273* (2013.01); *G01N 27/4045* (2013.01); *G01N 33/0006* (2013.01)

(58) Field of Classification Search
None
See application file for complete search history.

(56) References Cited

U.S. PATENT DOCUMENTS 5,053,064 A 10/1991 Hama et al.
5,823,044 A * 10/1998 Logothetis ......... G01N 33/0026
422/98

(Continued)

FOREIGN PATENT DOCUMENTS

CN 101571506 A 11/2009
CN 101776640 A 7/2010

(Continued)

OTHER PUBLICATIONS http://www.environmentalsensors.com/formaldehyde-monitor-z-300.html.

*Primary Examiner* — Michael A Lyons
*Assistant Examiner* — Jermaine Jenkins

(57) ABSTRACT

A method of selectively sensing the concentration of a target gas in polluted ambient air comprises the steps of: —providing a target gas sensor (220) sensitive to the target gas; —providing a first gas flow derived from the ambient air, from which first flow the target gas is substantially removed; —providing a second gas flow derived from the ambient air, substantially comprising the same target gas concentration as the ambient air; —exposing the target gas sensor to the first gas flow during a first time interval, and obtaining from the sensor a first output signal (Smf); —exposing the target gas sensor to the second gas flow during a second time interval not overlapping with the first time interval, and obtaining a second output signal (Smu); —calculating the difference (SΔ) between the first and the second output signals; calculating the concentration of the target gas from the calculated signal difference (SΔ).

15 Claims, 14 Drawing Sheets

(51) Int. Cl.
*G01N 19/10* (2006.01)
*G01N 27/403* (2006.01)
*G01N 1/22* (2006.01)
*G01N 27/404* (2006.01)
*G01N 33/00* (2006.01)

(56) References Cited

U.S. PATENT DOCUMENTS

| | | | | |
|---|---|---|---|---|
| 6,044,689 | A * | 4/2000 | Yoshida | G01N 27/12 422/93 |
| 6,071,479 | A | 6/2000 | Marra | |
| 6,736,001 | B1 * | 5/2004 | Mueller | G01N 27/12 422/94 |
| 8,910,506 | B2 * | 12/2014 | Johnson | A01G 7/00 73/23.2 |
| 2002/0092525 | A1 * | 7/2002 | Rump | A62B 9/006 128/205.23 |
| 2009/0113984 | A1 | 5/2009 | Gautieri et al. | |
| 2009/0211437 | A1 | 8/2009 | Fleischer | |
| 2013/0319110 | A1 * | 12/2013 | Otera | G01N 21/3504 73/335.01 |
| 2014/0007653 | A1 * | 1/2014 | Takasu | G01N 5/02 73/24.06 |
| 2014/0345363 | A1 * | 11/2014 | Pretre | G01N 25/18 73/25.03 |

FOREIGN PATENT DOCUMENTS

| | | |
|---|---|---|
| CN | 101825604 A | 9/2010 |
| JP | 2007139580 A | 6/2007 |
| RU | 2279066 C1 | 6/2006 |

* cited by examiner

GAS SENSING APPARATUS

CROSS-REFERENCE TO PRIOR APPLICATIONS

This application is the U.S. National Phase application under 35 U.S.C. §371 of International Application No. PCT/IB2012/053501, filed on Jul. 4, 2012, which claims the benefit of European Patent Application No. 11173728.4, filed on Jul. 13, 2011. These applications are hereby incorporated by reference herein.

FIELD OF THE INVENTION

The present invention relates in general to the field of gas sensors.

BACKGROUND OF THE INVENTION

An important application of gas sensors lies in the domain of indoor air pollution monitoring, only for obtaining objective data, and control of air handling units and/or air cleaning units. It would be desirable that such a sensor has the following features:

- small size;
- low cost;
- low power requirements;
- minimal maintenance requirements over an operational period of at least several years;
- a combination of high sensitivity and high selectivity with respect to a particular target gas or target class of gases.

Selectivity is especially important in situations where the composition of the gas to be measured is not known in advance. Lack of sufficient selectivity remains a key issue with all major sensor technologies and poses severe application problems in ordinary indoor environments where usually an unknown mixture of different gaseous pollutants is present.

A high selectivity towards a specific target gas or towards a specific class of target gases allows the obtained sensor signals to be interpreted unambiguously. This aspect also applies to the influence of the air humidity, the air temperature and the local air speed on the obtained sensor signals.

As regards the quality of ambient air, it is important to be able to unambiguously distinguish clean air from polluted air. Air may be polluted by a certain gas (for instance formaldehyde, $NO_x$, $O_3$, $SO_2$) or a certain class of gases (for instance the class of all volatile organic hydrocarbon gases, usually referred to as TVOC; or the class of acid gases, which includes $HNO_x$, $SO_2$ and organic carboxylic gases). Apart from the ability to detect whether a certain pollutant is present, it is also important to be able to detect the concentration of that pollutant. Air is considered to be unacceptably polluted with a certain target gas when the concentration of that target gas is comparable to or higher than its recommended maximum concentration limit. For indoor living environments, these so-called concentration limit standards are quite low, i.e. around 50 ppb for both $O_3$ and $NO_2$, 0.2-0.3 $mg/m^3$ for TVOC and 40 ppb for formaldehyde.

At present, no sensors or sensor technologies exist that fulfill all the above requirements to a satisfactory extent. Nevertheless, the use of metal-oxide semiconducting sensors or electrochemical sensors appears to be the most promising choice in this regard. This applies in particular to the sensing of formaldehyde, which is a recognized important air pollutant, in particular in Chinese residential environments.

However, an important problem with metal-oxide semiconducting sensors and electrochemical sensors is their lack of selectivity. Several attempts to overcome this problem have already been proposed.

The gas to be examined, for instance ambient air, may contain several pollutants, and it would be desirable to be able to measure the concentration of each one of these pollutants individually. However, pollutants tend to influence measurements directed at other pollutants. In a basic approach, it is attempted to eliminate all "other" pollutants, so that only one pollutant (i.e. the target gas) remains: a sensor output signal obtained from the thus filtered gas will be proportional to the amount of (concentration of) target gas. Such an approach to try to improve the sensing selectivity of a gas sensor is described in for instance CN101825604 and CN101776640. These documents propose to specifically remove the interfering gases from air with a "scrubbing filter".

A disadvantage of this approach is that it requires knowledge of the identity of the "other" pollutants. However, it is usually not a priori known which gaseous pollutants interfere and the extent to which they interfere with the measurement of the target gas. Furthermore, gases of widely different physical properties such as $H_2$ and ethanol are known to be interfering gases for electrochemical formaldehyde sensors and it is far from easy to effectively remove all these gases from air at room temperature using small low-cost passive filters. It is therefore in general very difficult or even impossible to design a practical filter capable of removing all interfering gases from air while leaving everything else the same. Another approach, therefore, is to have a filter for removing the target gas from the polluted air, and to perform two measurements: one measurement on the original polluted air, which still comprises the target gas, and one measurement on the original polluted air from which the target gas has been removed. The difference between the two measurement signals obtained in these two measurements will be proportional to the amount of (concentration of) the target gas.

A company by the name of "Environmental Sensors" has recently proposed a portable electrochemical formaldehyde sensor equipped with a removable formaldehyde sheet filter impregnated with a chemical reactant capable of specifically removing formaldehyde from the ambient air entering the sensor interior (see http://www.environmentalsensors.com/formaldehyde-monitor-z-300.html). The formaldehyde filter furthermore serves as a diffusion barrier which limits the entry of gaseous species into the electrochemical cell. This formaldehyde filter can be manually replaced by a blank filter, which only serves as a diffusion barrier and which hence does not absorb any gases from air. By comparing the obtained sensor signal in the presence of the formaldehyde filter with the sensor signal in the presence of the blank filter, a signal difference is obtained that is directly proportional to the formaldehyde concentration, since the influence of other (interfering) gaseous pollutants is excluded.

A disadvantage of this approach is that the two filters can only be exchanged manually, which is inconvenient. Furthermore, the used filter is embodied as a flat fibrous sheet filter, which can be impregnated with only a very limited amount of the reactant that removes formaldehyde from air. The useful lifetime of the formaldehyde filter is therefore only short and not practical in ordinary indoor environments. It is furthermore unknown when the used formaldehyde sheet filter should be replaced. In addition, the impregnation of the fibrous sheet filter with the reactant material results in an inevitable reduction of the filter porosity, thereby changing its diffusion barrier characteristics. The latter characteristics are furthermore dependent on the ambient humidity because of the humidity-dependent moisture uptake by the reactant. The afore-mentioned circumstances result in serious interpretation difficulties with respect to the obtained signal difference in terms of the ambient formaldehyde concentration and lead to large inaccuracies.

Yet another approach to try to improve the sensing selectivity of a gas sensor is described in for instance CN101571506 (Huarui Scientific Instrument Shanghai). This document proposes an electrochemical formaldehyde sensor comprising a first working electrode, a compensation electrode, and a common counter electrode. The compensation electrode effectively acts as a second working electrode characterized in that it is provided with a filter capable of specifically removing formaldehyde from air. The formaldehyde filter furthermore acts as a general gas diffusion barrier. The first working electrode is provided with a dummy filter and only acts as a gas diffusion barrier. By subtracting the sensor signal obtained from the first working electrode (having contributions from both formaldehyde and interfering gases) from the signal obtained from the compensation electrode (having contributions from only the interfering gases), a differential signal is obtained that only accounts for the formaldehyde concentration in air and compensates for possible effects related to humidity and temperature changes.

A disadvantage of the solution offered by Huarui is that effectively two separate working electrodes are needed within a single electrochemical sensor, as illustrated in FIG. 1. Small physical differences between the two working electrodes can easily lead to quite different sensor responses and different signal bias, both with respect to their zero readings (in clean air) and with respect to their span (the signal difference per unit concentration of the target gas and/or of the interfering gases). It is therefore generally difficult, if not impossible, to unambiguously interpret the obtained differential sensor signal in terms of the target gas concentration. Because the filters are integrated within the electrochemical sensor, it is not feasible to remove or otherwise manipulate them, for instance for sensor calibration purposes.

SUMMARY OF THE INVENTION

An object of the present invention is to overcome or at least reduce the above problems.

To meet this objective, the present invention proposes a method and a sensing arrangement for determining the concentration of a target gas in ambient air. The sensing arrangement comprises a target gas sensor, a target gas filter, means for air displacement through the sensing arrangement, a controller capable of controlling the means for air displacement, and an evaluation unit capable of receiving and interpreting output signals from the target gas sensor. The target sensor is exposed to a first gas flow of displaced air, wherein the target gas concentration is substantially the same as in the polluted ambient air. The target sensor is exposed to a second gas flow of displaced air which comprises substantially the same pollution as the first gas flow of displaced air except that the target gas has substantially been removed from the second gas flow of displaced air through selective filtration by the target gas filter. The difference between the correspondingly obtained sensor output signals is then proportional to the concentration of the target pollutant only, thus enabling selectivity. An advantage of this method and apparatus is that it requires only one gas sensor.

Further advantageous embodiments and elaborations are mentioned in the dependent claims.

The present invention also proposes an embodiment of a sensing arrangement in which two separate gas sensors are used for obtaining a differential signal that is characteristic of the concentration of the target gas, and in which means are provided to equalize the respective sensor responses when the two sensors are exposed to the same gaseous environment. The latter possibility at least partly compensates for possible differences in the measured sensor responses of the two sensors as a function of the target gas concentration, the concentrations of the respective interfering gases, the temperature and the relative humidity.

BRIEF DESCRIPTION OF THE DRAWINGS

These and other aspects, features and advantages of the present invention will be further explained by means of the following description of one or more preferred embodiments with reference to the drawings, in which same reference numerals indicate same or similar parts, and in which.

DETAILED DESCRIPTION OF THE INVENTION

Figure 1:
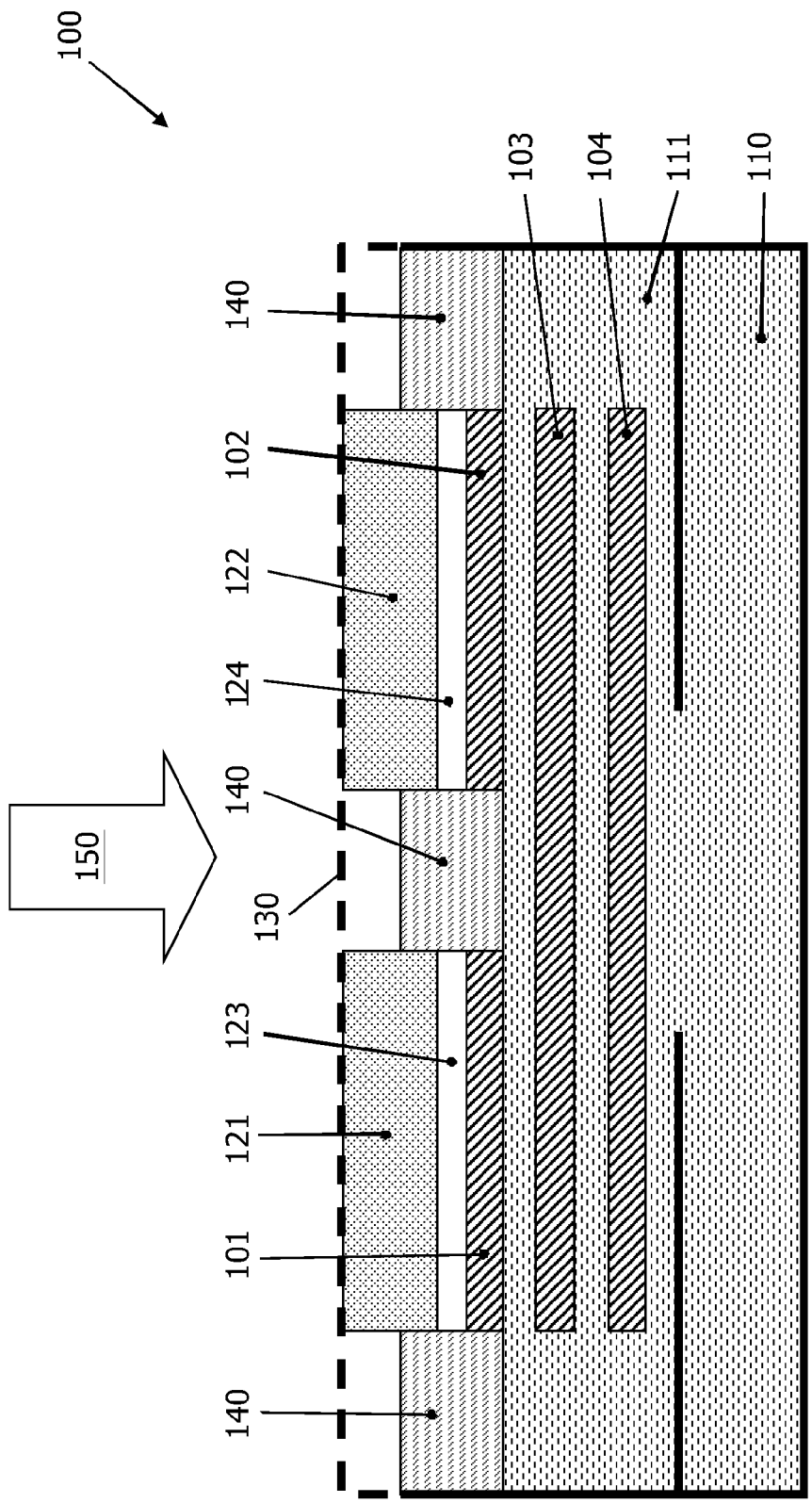
FIG. 1 schematically shows a prior art electrochemical sensor.

FIG. 1 schematically shows a prior art electrochemical sensor 100 comprising a first working electrode 101, a second working electrode 102, a reference electrode 103, and a common counter electrode 104. Both working electrodes 101 and 102 share the same counter electrode 104 and the same reference electrode 103 and are exposed to the same electrolyte solution 111 from an electrolyte reservoir 110.

Over the first working electrode 101, a filter 121 for a specific target gas is arranged. This filter 121 effectively removes the target gas from an airflow. An air gap between the filter 121 and the first working electrode 101 is indicated at 123. Over the second working electrode 102, a dummy filter structure 122 is arranged. This structure 122 has mechanical properties similar to filter 121, but does not filter out any of the air pollutants. An air gap between the dummy filter structure 122 and the second working electrode 102 is indicated at 124. Insulators adjacent the working electrodes are indicated by reference numerals 140. An air-permeable sensor cover 130 covers the filter 121 and the dummy filter structure 122 and holds them in place.

The gas to be monitored, for instance ambient air 150, slowly passes the cover 130 and the filter 121 or the dummy filter structure 122, respectively, to reach the first working electrode 101 or the second working electrode 102, respectively. Thus, the first working electrode 101 is passively exposed to air from which the target pollutant has been removed, while the second working electrode 102 is passively exposed to unfiltered ambient air. If the two working electrodes 101, 102 have mutually equal characteristics, the difference between their output signals is proportional to the amount (or concentration) of target gas in the air.

Figure 2:
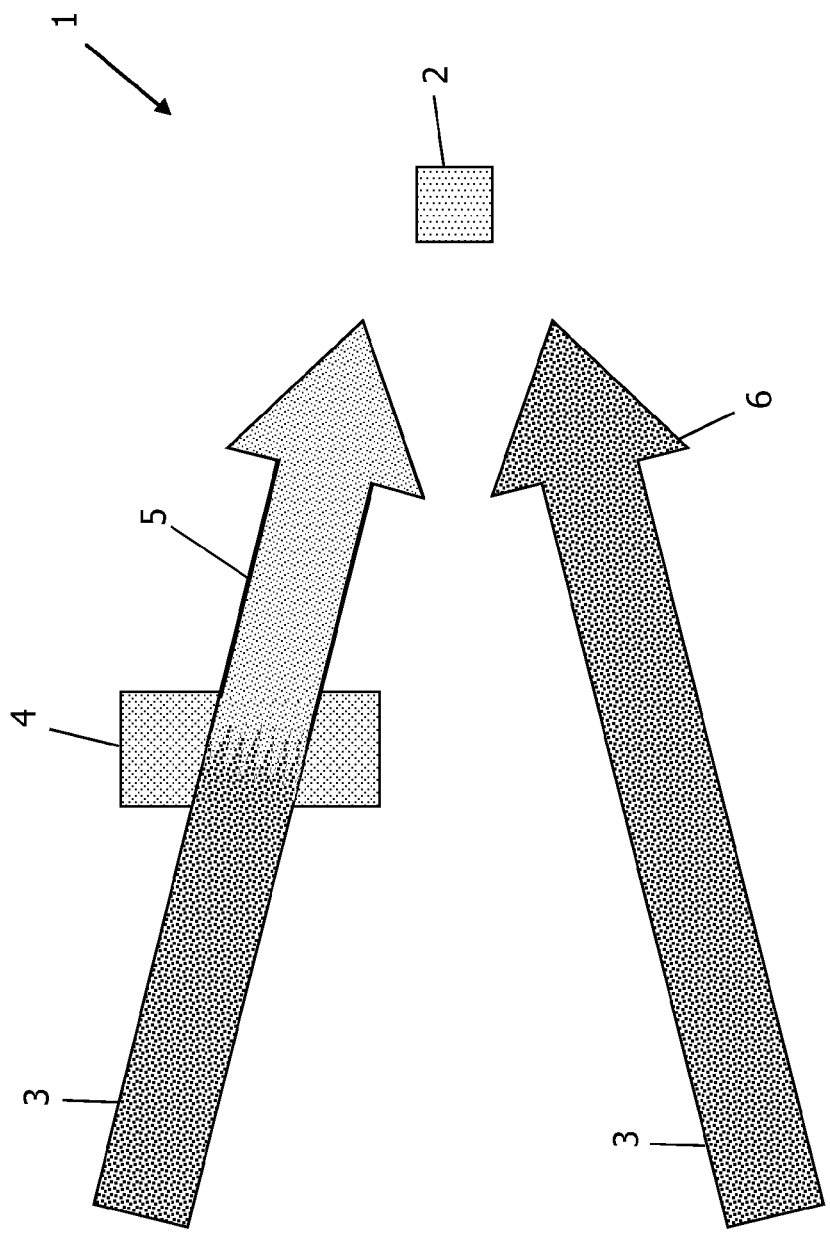
FIG. 2 shows the sensor exposure to two possible flows of displaced air, wherein one flow first passes the target gas filter before reaching the sensor.

FIG. 2 is a drawing schematically illustrating the basic principles behind the present invention. A gas sensing apparatus according to the present invention is generally indicated by reference numeral 1, and comprises a gas sensor 2 and a target gas filter 4. As long as it is sensitive to at least the target gas to be sensed, the gas sensor 2 may be any known sensor; therefore a more detailed description of the gas sensor 2 is omitted here. It is noted that the gas sensor 2 as such does not need to have selectivity for the target gas. In fact, the gas sensor may be sensitive to various different target gases or classes of target gases.

The apparatus 1 furthermore comprises controllable means capable of causing air 3, derived from polluted ambient air, to follow either one of at least two different airflow paths, as illustrated by two flow arrows 5 and 6. The concentration of the target gas in air 3 is substantially the same as in the ambient air from which air 3 is derived. In one airflow 5, the air 3 passes the target gas filter 4, so that the target gas is substantially removed from the air 3 before the air reaches the sensor 2. In another airflow 6, the air 3 does not pass the target gas filter 4, so that the airflow 6 reaching the sensor 2 has substantially the same concentration of target gas as the ambient air. The air 3 may be totally unfiltered ambient air, so that the composition of air 6 is substantially equal to the composition of ambient air. It is also possible that air 3 is derived from ambient air by passing the ambient air through a filter that removes one or more gas components but does not affect the concentration of the target gas. This means that both gas flows 5 and 6, when reaching the sensor 2, have the same composition as far as all other components are concerned, except for the target gas which is substantially absent in the first gas flow 5 and which is substantially present in the second gas flow 6 to the same extent as in the original ambient air. Thus, the sensor is exposed either to air WITH or air WITHOUT the target gas, all other components being the same, and any difference in the sensor output signal in these two situations is representative of the amount of target gas.

Several implementations are possible, as will be explained in the following. For allowing unfiltered ambient air 6 to reach the gas sensor 2, it may be sufficient to use (natural) convection as the driving force for air displacement, but it is also possible to use airflow generating means, for instance a ventilator or a pump. For making air pass the filter 4, convection will usually be insufficient to generate the airflow 5, so that the apparatus preferably comprises airflow generating means, for instance a ventilator, but it is also possible to connect the apparatus to a source of pressure difference. Airflow selection in the gas sensing apparatus 1 can for instance be done by using controllable valves and/or controllable ventilators.

Figure 3A:
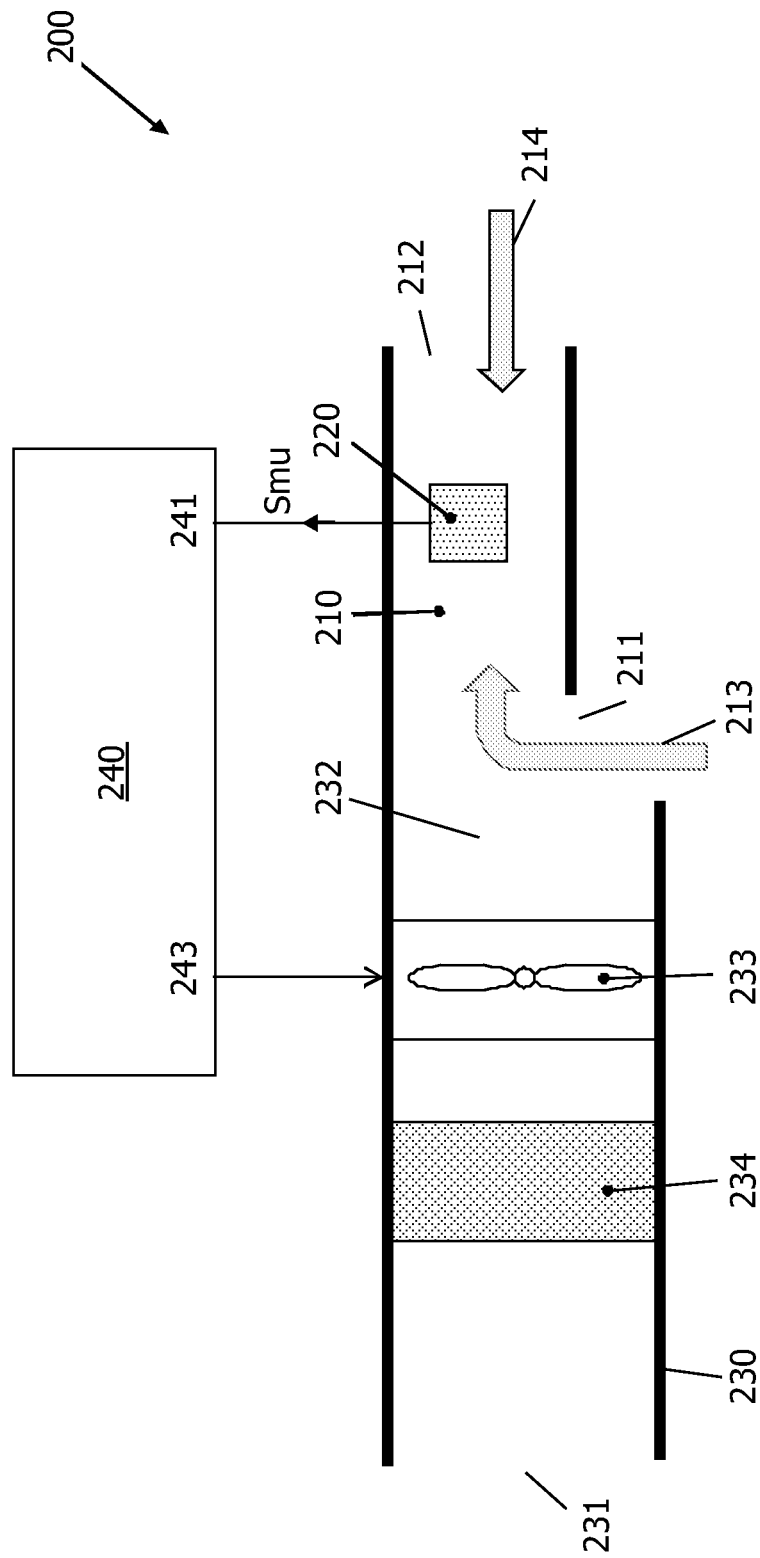
FIGS. 3A-3C schematically illustrate a first embodiment of a gas sensing apparatus according to the present invention.
Figure 3B:
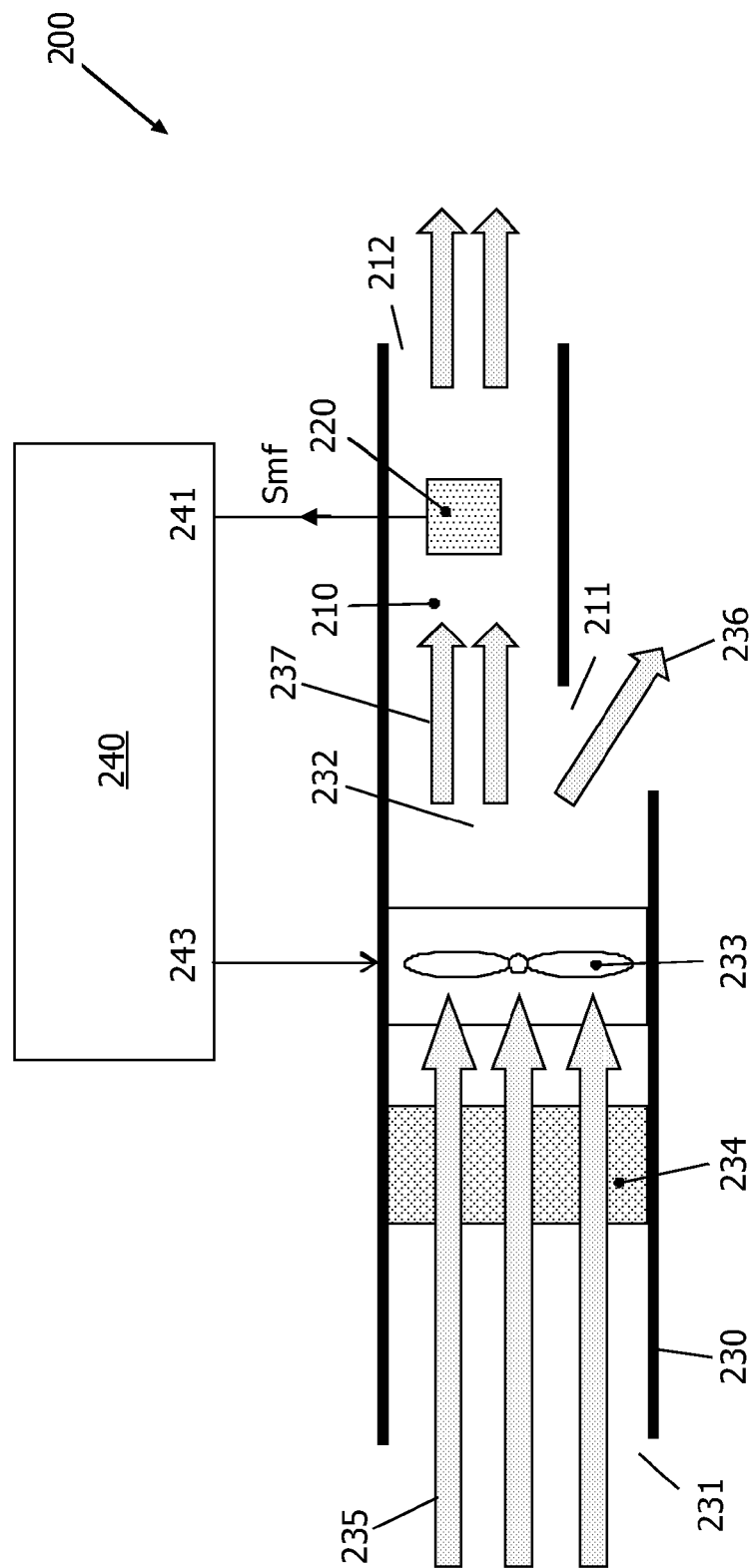

A first embodiment of a gas sensing apparatus according to the present invention is generally indicated by reference numeral 200 and is schematically illustrated in FIGS. 3A and 3B. The gas sensing apparatus 200 comprises a measuring chamber 210 and a gas sensor 220 arranged in the measuring chamber 210.

The measuring chamber 210 has at least one passageway 211 allowing direct entry of ambient air and allowing this ambient air to reach the measuring chamber 210 unfiltered. In the embodiment shown, there are two different passageways 211, 212 connecting the measuring chamber 210 to the ambient environment such as to allow for convection.

The gas sensing apparatus 200 further comprises an air duct 230 having an entrance 231 communicating with the ambient environment and an output 232 communicating with the measuring chamber 210. The gas sensing apparatus 200 further comprises a gas filter 234 and a controllable airflow generating means 233, for instance a ventilator, arranged in the air duct 230. The figure shows the gas filter 234 arranged between the entrance 231 and the ventilator 233, but this order may also be reversed. The filter 234 is selected for substantially removing the target gas to be sensed from any air passing the filter, and will also be indicated as target gas filter.

The gas sensing apparatus 200 further comprises a control device 240 for controlling the ventilator 233, the control device 240 having a control output 243 coupled to a control input of the ventilator 233. The control device 240 may for instance be implemented as a suitably programmed microprocessor, microcontroller, or the like. The control device 240 in this embodiment is integrated with means for sensor signal evaluation, for which purpose the control device 240 is provided with a measuring input 241 connected to receive an output signal from the sensor 220. It is noted that the functionality of sensor signal evaluation may be implemented in a different unit, which then would have an output communicating with an input of the control device, so that control of the ventilator can take place on the basis of the outcome of the sensor signal evaluation.

The gas sensing apparatus 200 is capable of operating in two different operational modes. In a first operational mode, the gas sensor 220 is exposed to unfiltered ambient air: this mode will hereinafter be indicated as "unfiltered mode", and the measuring output signal of the sensor 220 in this mode will be indicated as Smu. In a second operational mode, the gas sensor 220 is exposed to a flow of ambient air filtered by the filter 234: this mode will hereinafter be indicated as "filtered mode", and the measuring output signal of the sensor 220 in this mode will be indicated as Smf. The control device 240 is capable of calculating a differential signal SΔ=Smu−Smf, which is proportional to the target gas concentration in the unfiltered ambient air. This differential signal SΔ can be considered as constituting the measuring output signal of the sensing apparatus 200. It is noted that the tasks of receiving and processing the sensor output signals on the one hand and controlling the ventilator on the other hand may alternatively be performed by separate calculating/evaluating and control units.

FIG. 3A illustrates the gas sensing apparatus 200 operating in its unfiltered mode. The ventilator 233 is off. Convective flows of unfiltered ambient air 213, 214 reach the measuring chamber 210 through the passageways 211, 212.

FIG. 3B illustrates the gas sensing apparatus 200 operating in its filtered mode. The ventilator 233 is on, causing a flow of ambient air 235 in the duct 230 to pass the filter 234 and reach the measuring chamber 210 as filtered air 237, leaving the measuring chamber 210 via passageway 212 which now acts as an output.

Preferably, the control device 240 switches the ventilator 233 on and off periodically, such as to periodically alternate between the filtered mode and the unfiltered mode.

Figure 3C:
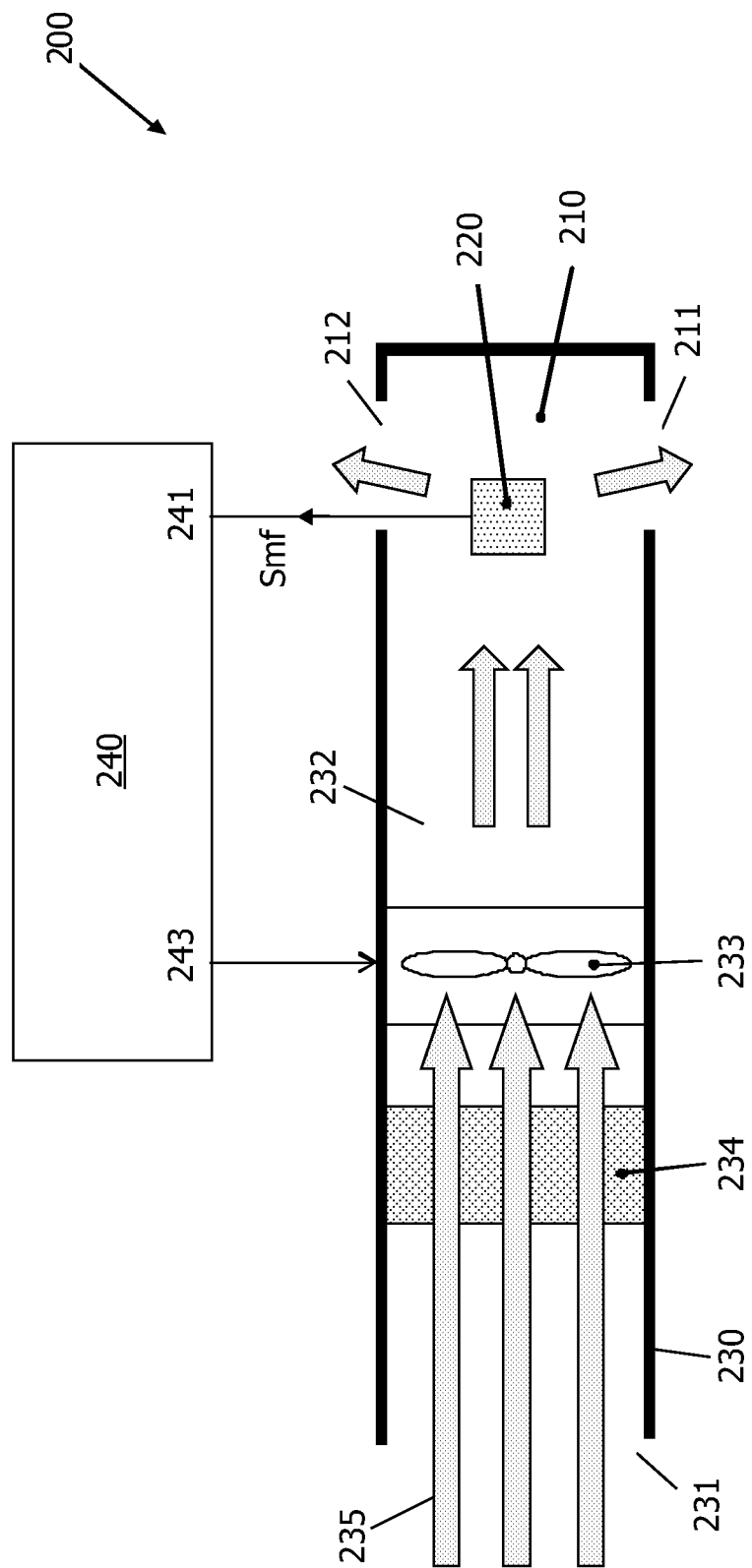

In the schematical layout of FIGS. 3A and 3B, the first passageway 211 is shown between the duct 230 and the measuring chamber 210. In such a case, the design should be such that a portion 236 of the flow 235 generated in the duct 230 is blown out through the first passageway 211 in order to prevent unfiltered ambient air from reaching the measuring chamber 210. FIG. 3C illustrates a layout where this issue does hardly play a role.

In the above, it has been mentioned that, in the unfiltered mode, unfiltered ambient air may reach the sensor convectively, i.e. with the ventilator off. Alternatively, it is possible that the gas sensing apparatus 200 comprises a second ventilator for, in the unfiltered mode, causing a flow of unfiltered ambient air to enter the measuring chamber 210 through one passageway 211 and leave the measuring chamber through the other passageway 212, or vice versa.

Figure 4:
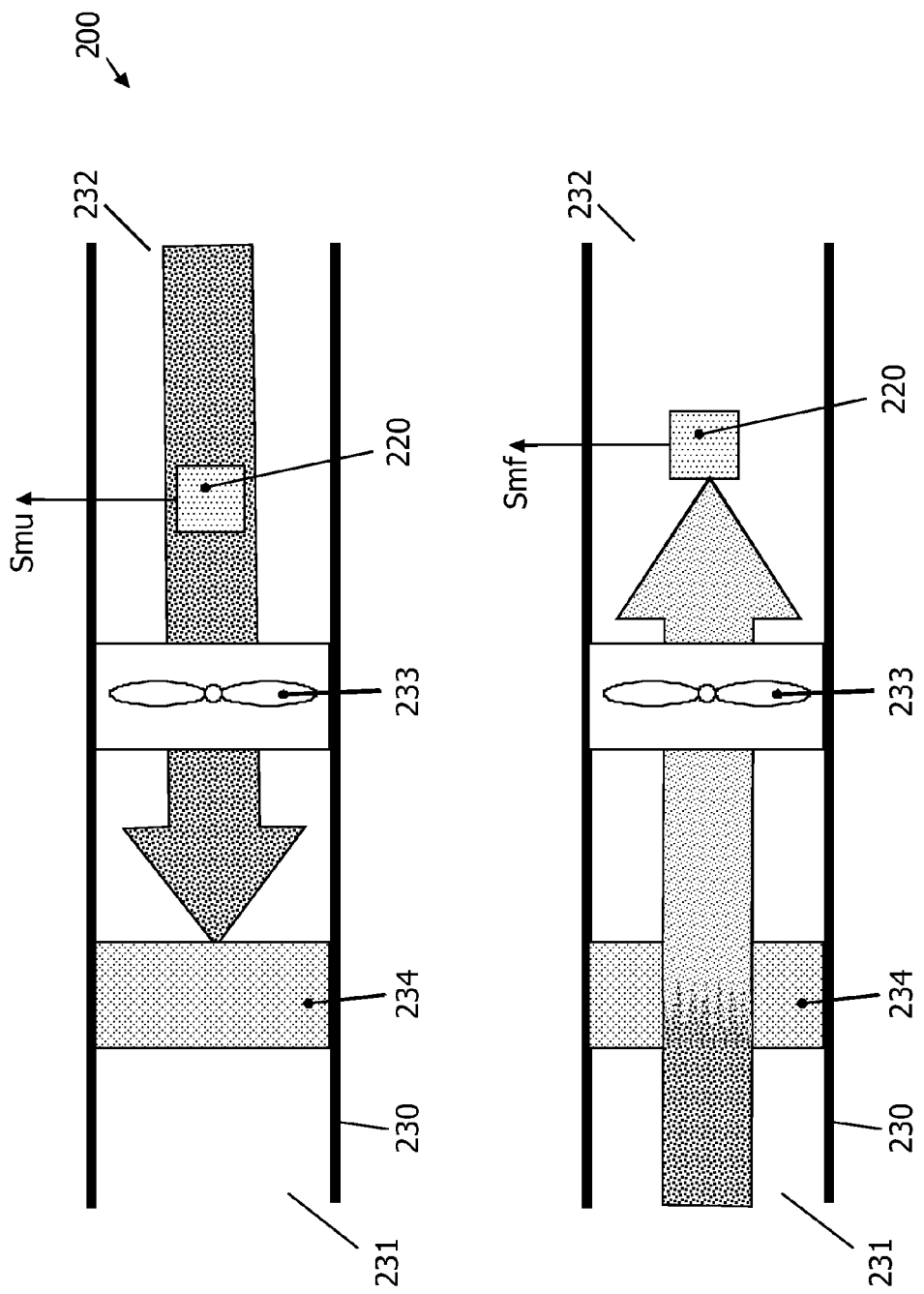
FIGS. 4-9 schematically illustrate several variations of embodiments of a gas sensing apparatus according to the present invention, requiring only a single target gas sensor.

In the above, switching between the filtered operational mode and the unfiltered operational mode is done by switching the ventilator 233 on or off. It is also possible to obtain such switching by selectively operating the ventilator 233 in one direction or an opposite direction, as illustrated in FIG. 4. The duct 230 is shown to have two input/output openings 231, 232 with the sensor 220, ventilator 233 and filter 234 being arranged between said openings. In the upper half of the figure, the ventilator 233 is operated to generate an airflow from the right to the left, so that the sensor 220 is upstream of the filter 234: the airflow reaches the sensor 220 before reaching the filter 234. This is the unfiltered mode, wherein the sensor 220 is exposed to unfiltered air and outputs the unfiltered output signal Smu. In the lower half of the figure, the ventilator 233 is operated to generate an airflow from the left to the right, so that the sensor 220 is downstream of the filter 234: the airflow reaches the filter 234 before reaching the sensor 220. This is the filtered mode, wherein the sensor 220 is exposed to filtered air and outputs the filtered output signal Smf.

It is noted that the relative position of the ventilator 233 is not essential: it may be located between opening 231 and the filter 234, between opening 232 and the sensor 220, or between filter 234 and sensor 220. It is further noted that, instead of a bi-directional ventilator, two mono-directional ventilators can be used, arranged in mutually opposite orientation.

Figure 5:
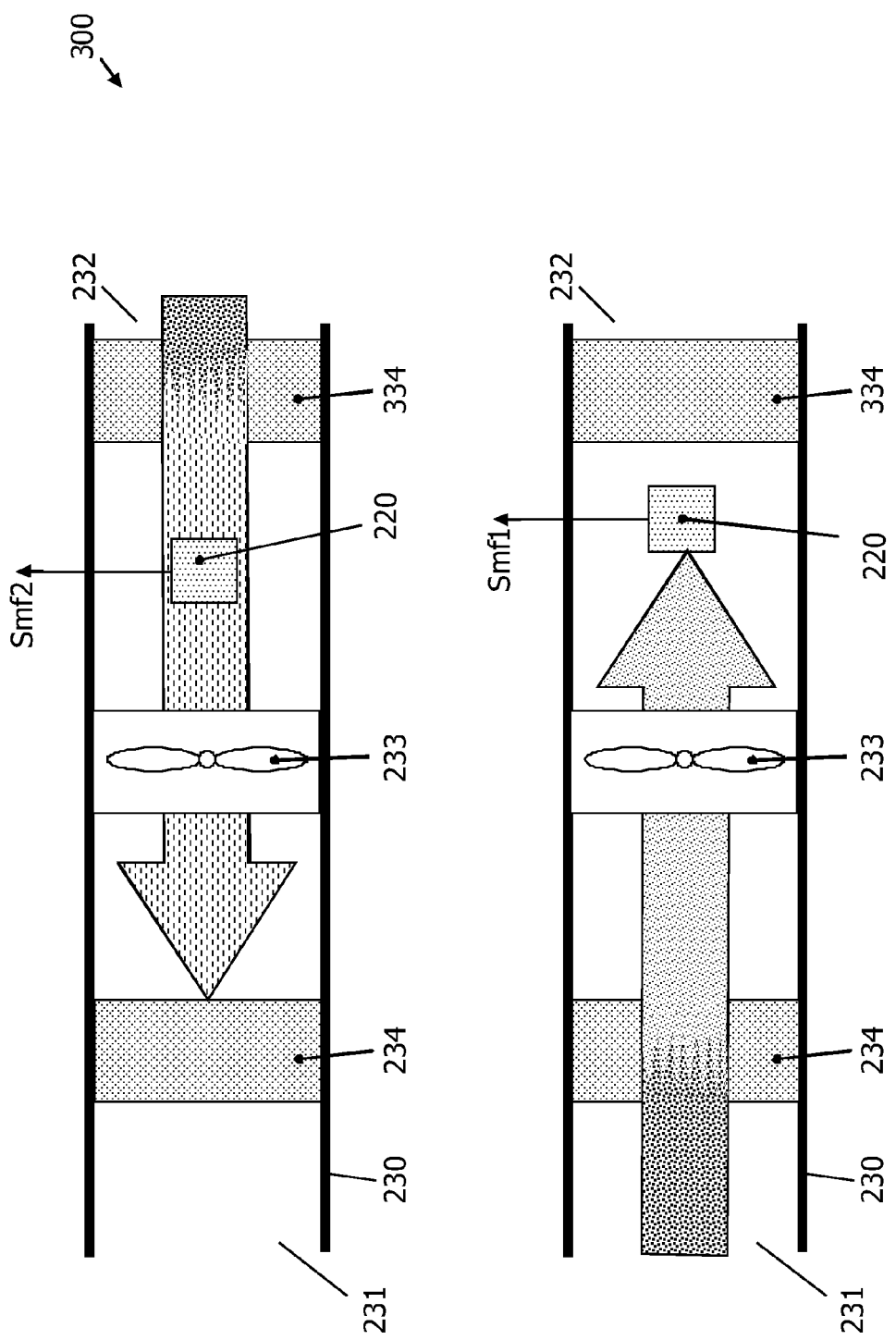

In a further elaboration, illustrated in FIG. 5, apparatus 300 has two different filters 234 and 334 arranged on opposite sides of the sensor 220. Again, the relative position of the ventilator 233 is not essential. The second filter 334 has filtering characteristics differing from the first filter 234 in that it does not filter the target gas. More particularly, the second filter 334 is capable of filtering a specific gas or group of gases or class of gases, and the first filter 234 is capable of filtering the same specific gas or group of gases or class of gases, respectively, as well as the target gas.

In the lower half of FIG. 5, the situation is equivalent to the situation of FIG. 4 (lower half): the second filter 334 is downstream of the sensor 220 and has no influence on the sensor output signal Smf1. In the upper half of the figure, with the reverse flow direction, the second filter 334 is upstream of the sensor 220, so that the airflow reaches the second filter 334 before reaching the sensor 220; the sensor output signal in this case is indicated as Smf2. In both cases, the sensor 220 is exposed to filtered gas. In both cases, said specific gas or group of gases or class of gases, respectively, has been removed from the original ambient gas. In the case of the lower half of the figure, with the first filter 234 upstream of the sensor 220, also the target gas has been removed. Consequently, a difference signal SΔ'=Smf2−Smf1 is proportional to the target gas concentration in the filtered gas and therefore proportional to the target gas concentration in the unfiltered ambient gas. This embodiment is advantageous in cases where it is desirable to protect the sensor 220 against the influence of certain gases.

Figure 6:
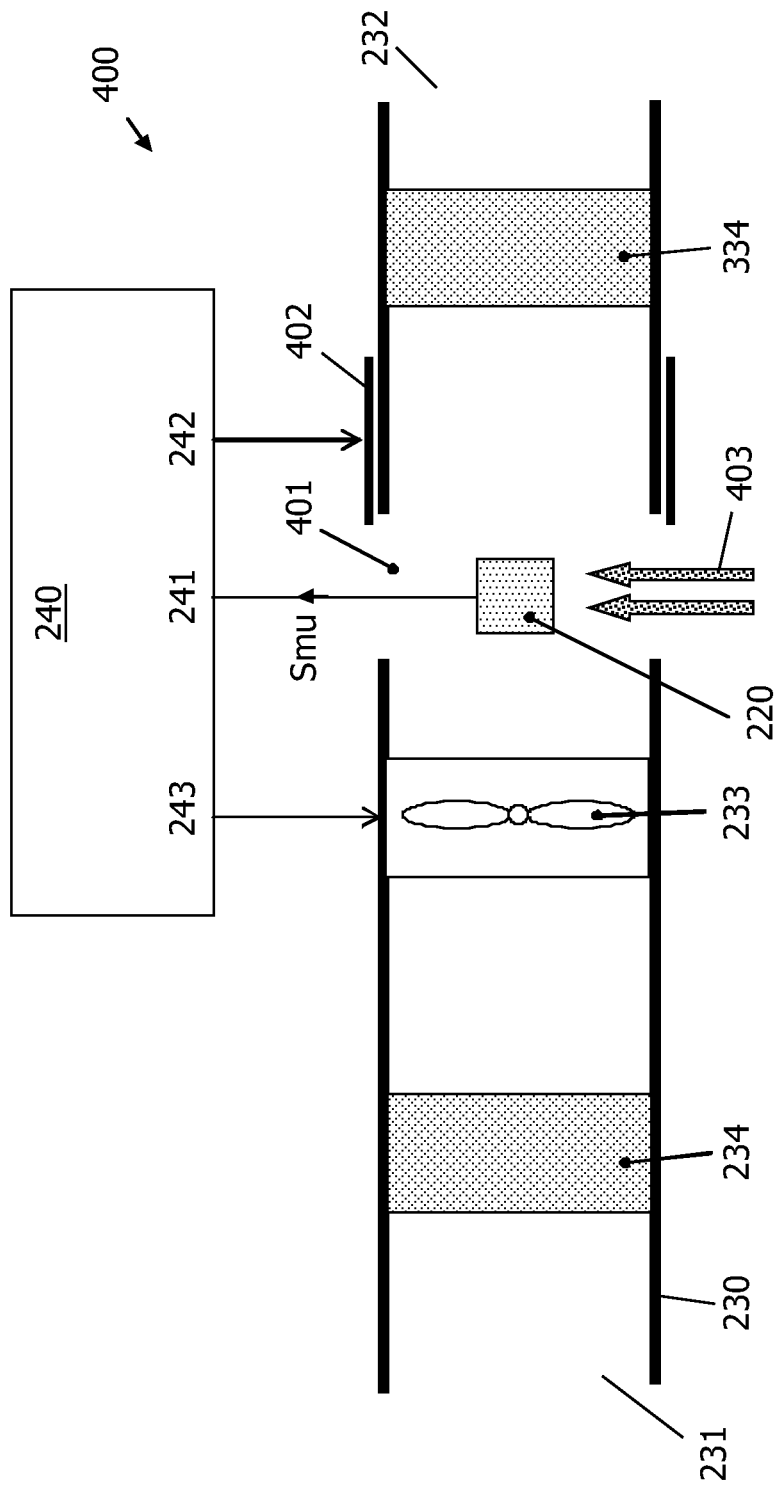

In a further elaboration, illustrated in FIG. 6, the duct 230 of apparatus 400 has one or more openings 401 allowing ambient gas 403 to directly reach the sensor 220 without being filtered. The one or more openings 401 is/are provided with controllable closure means 402 controlled by the control device 240 at its output 242. With the controllable closure means 402 in the closed state, the situation is basically identical to the situation of apparatus 300 in FIG. 5 and the target gas concentration can be inferred from the signal difference SΔ'=Smf2−Smf1. The control device 240 now has the additional option of switching the ventilator 233 off and opening the closure means 402 in order to allow ambient gas 403 to directly reach the sensor 220, for instance through convection. The sensor 220 now provides a measuring signal Smu derived from unfiltered ambient gas, and it is possible to calculate a difference signal SΔ"=Smu−Smf2 proportional to the concentration of said specific gas or group of gases or class of gases, respectively. In other words, apparatus 400 is selective to two different gases or two different groups of gases independently of each other, and these can be inferred by the apparatus 400 from the signal differences SΔ'=Smf2−Smf1 and SΔ"=Smu−Smf2, respectively. It will be clear that in this embodiment the gas sensor 220 should have sufficient sensitivity to both different gases or to both different groups of gases in order to achieve selectivity to both different gases or to both different groups of gases, independently of each other, at the respective concentrations thereof in the ambient air.

Figure 7:
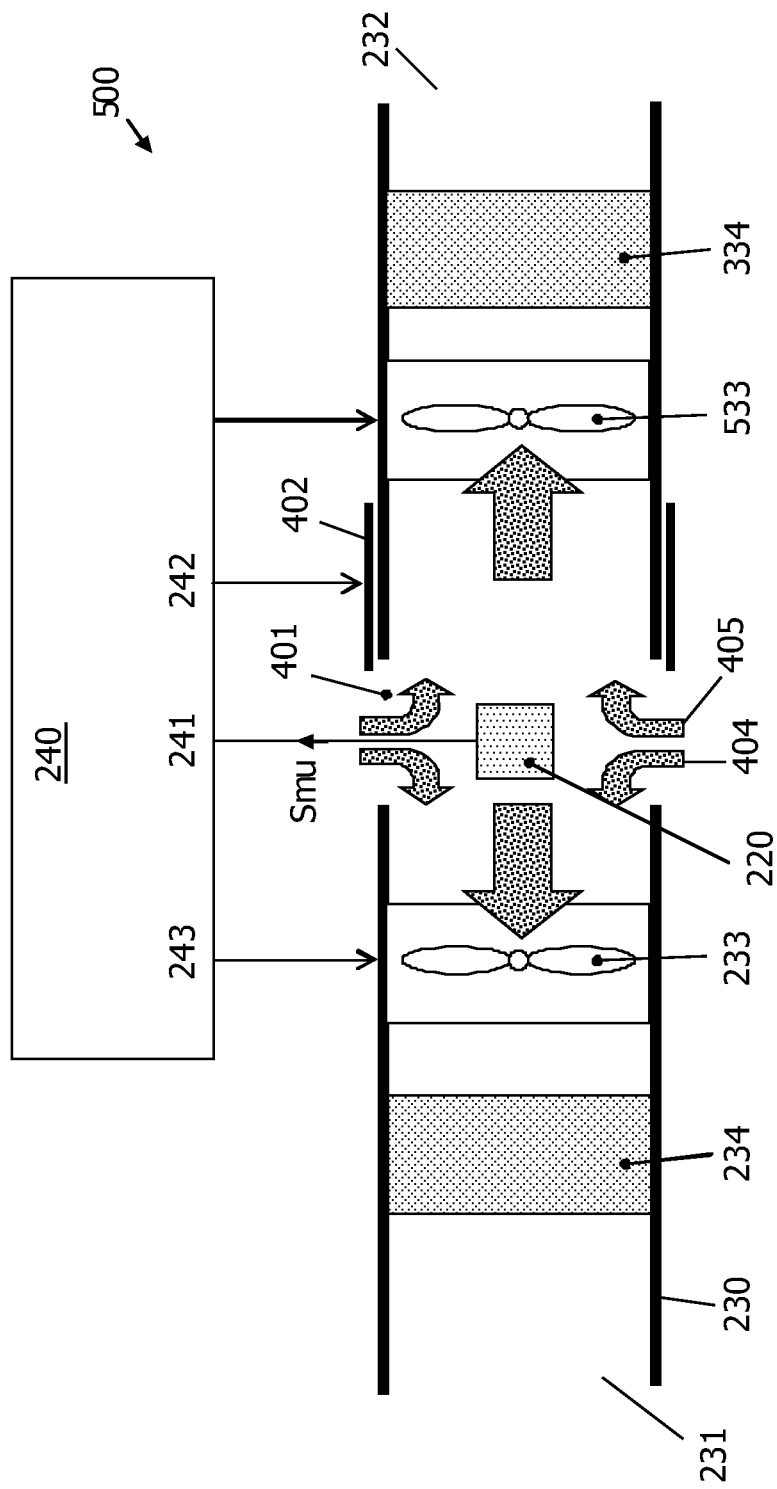

In a further elaboration, illustrated in FIG. 7, the apparatus 400 has a series arrangement of first filter 234 and first ventilator 233 arranged on one side of the sensor 220, wherein the relative order of the first filter 234 and first ventilator 233 is not essential, and has a series arrangement of second filter 334 and a second ventilator 533 arranged on the opposite side of the sensor 220, wherein the relative order of the second filter 334 and second ventilator 533 is not essential. Both ventilators may be bi-directional ventilators, but that is not essential. The control device 240 again has the option of switching off both ventilators 233, 533: the situation then is equivalent to the situation of FIG. 6, where ambient gas 403 is allowed to directly reach the sensor 220 through convection. The control device 240 now has the additional option of switching on both ventilators 233, 533 to generate a first forced airflow 404 from opening 401 towards first filter 234 and a second forced airflow 405 from opening 401 towards second filter 334. Consequently, ambient gas is actively forced to pass the sensor 220, and the unfiltered measuring signal Smu is obtained without being dependent on convection.

With reference to FIG. 5, it is noted that the first filtered output signal Smf1 can now be obtained by closing the closure means 402 and operating one or both ventilators 233, 533 to create an airflow from the left to the right in the figure, so that effectively the situation is equivalent to the situation of the lower half of FIG. 5, and it is further noted that the second filtered output signal Smf2 can now be obtained by closing the closure means 402 and operating one or both ventilators 233, 533 to create an airflow from the right to the left in the figure, so that effectively the situation is equivalent to the situation of the upper half of FIG. 5. Alternatively, however, it is possible to obtain the first filtered output signal Smf1 by opening the closure means 402, switching off the second ventilator 533 and operating the first ventilator 233 to create an airflow from the left to the right in the figure, exiting via the opening 401, and it is possible to obtain the second filtered output signal Smf2 by opening the closure means 402, switching off the first ventilator 233 and operating the second ventilator 533 to create an airflow from the right to the left in the figure, exiting via the opening 401.

In the above description with reference to FIGS. 4-7, the sensor 220 is described as being arranged in a "duct" 230 having input/output openings 231, 232 at opposite sides of the sensor. However, with reference to FIGS. 3A-D, it is also possible to describe such an arrangement as being a combination of two ducts, each having one input/output opening communicating with the ambient atmosphere and an opposite input/output opening communicating with a location where the sensor is positioned, such a location being referred to as measuring chamber. In the following description with reference to FIG. 8, the latter wording will be used for the sake of convenience.

Figure 8:
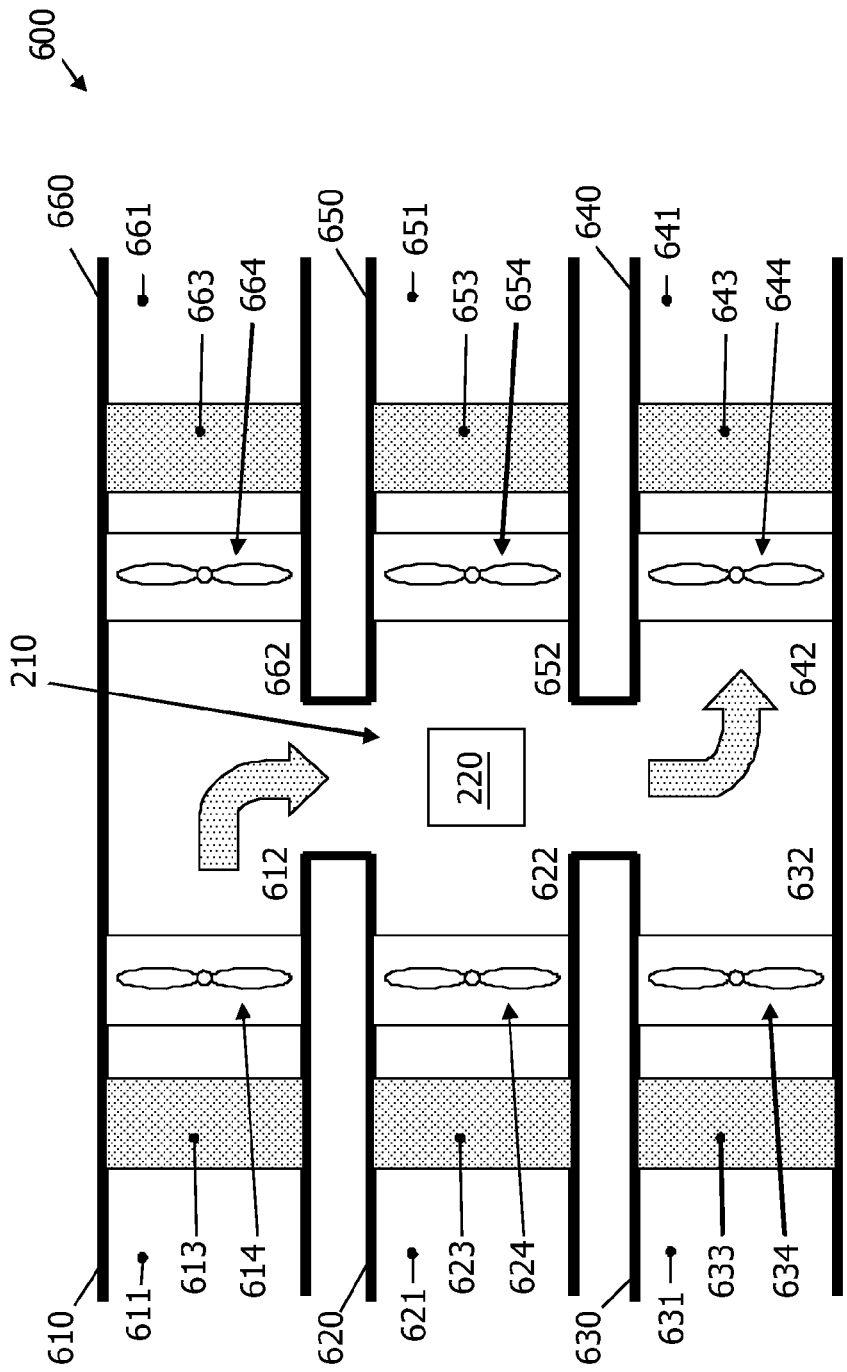

Apparatus 600 of FIG. 8 is a further elaboration of apparatus 500 of FIG. 7, illustrating that it is possible to effectively have multiple apparatuses 500 sharing one common sensor 220 arranged in a measuring chamber 210. The figure shows an embodiment with six ducts 610-660, each duct having a first opening 611-661 communicating with the ambient atmosphere and an opposite opening 612-662 communicating with the measuring chamber 210. In each duct 610-660, a series arrangement of a filter 613-663 and a bi-directional ventilator 614-664 (or other type of flow generator) is arranged. The ventilators are controlled by a control device not shown in this figure for the sake of simplicity. With reference to FIGS. 6 and 7, it is noted that this apparatus 600 may also comprise an opening for allowing ambient gas to reach the measuring chamber 210, either through convection (as in FIG. 6) or through suction by operating all ventilators (as in FIG. 7).

The six ducts 610-660 together define three pairs of ducts 610, 640; 620, 650; 630, 660. The ducts of each pair are arranged in such a way that their respective second openings 612, 642; 622, 652; 632, 662 are located on opposite sides of the measuring chamber 210. The control device is designed such as to selectively operate one of said pairs of ducts, with the other pairs being out of operation. Then, such a selected pair of ducts behaves like the embodiment 300 discussed with reference to FIG. 5. FIG. 8 illustrates this for the ducts 610 and 640: by appropriate control of the corresponding ventilators 614, 644, ambient air flows from opening 611 via measuring chamber 210 towards opening 641, as shown by arrows, or in the opposite direction, so the sensor 220 is exposed to air selectively filtered by either filter 613 or filter 643, respectively. Likewise, the ducts 620 and 650 form an associated pair: by appropriate control of the corresponding ventilators 624, 654, ambient air flows from opening 621 via measuring chamber 210 towards opening 651, or in the opposite direction, so the sensor 220 is exposed to air selectively filtered by either filter 623 or filter 653, respectively. Likewise, the ducts 630 and 660 form an associated pair: by appropriate control of the corresponding ventilators 634, 664, ambient air flows from opening 631 via measuring chamber 210 towards opening 661, or in the opposite direction, so the sensor 220 is exposed to air selectively filtered by either filter 633 or filter 663, respectively.

It should be clear that the same type of operation applies if the number of such pairs is equal to 2 or equal to 4 or more.

It is further noted that FIG. 8 shows all the ducts as being in open communication with the ambient atmosphere. However, in order to avoid an undesired airflow through any of the inactive ducts, each duct is preferably equipped with a controllable closure device, for instance a valve, controlled by the control device, which controls the closure devices such that the closure devices of the inactive ducts are always closed and the closure devices of the active ducts are always open.

In each pair of associated ducts (for instance 610, 640), the corresponding pair of filters (for instance 613, 643) is designed in the same way as in the apparatus 300 described with reference to FIG. 5. Thus, one filter of this pair of filters (for instance 613) is capable of filtering a specific gas or group of gases or class of gases, and the other filter of this pair of filters (for instance 643) is capable of filtering the same specific gas or group of gases or class of gases, respectively, as well as the target gas. When comparing different pairs of associated ducts with each other, the design of the corresponding pairs of filters differs because either the target gas of one pair of filters differs from the target gas of the other pair of filters, or the specific gas or group of gases or class of gases of one pair of filters differs from the specific gas or group of gases or class of gases of the other pair of filters, or both. Thus, by suitable activation of the several ventilators, it is possible to obtain individual information on the concentration of multiple gases separately while using only one sensor, provided that the sensor has non-zero sensitivity towards each of the said multiple gases at their respective concentrations in the ambient air.

Figure 9:
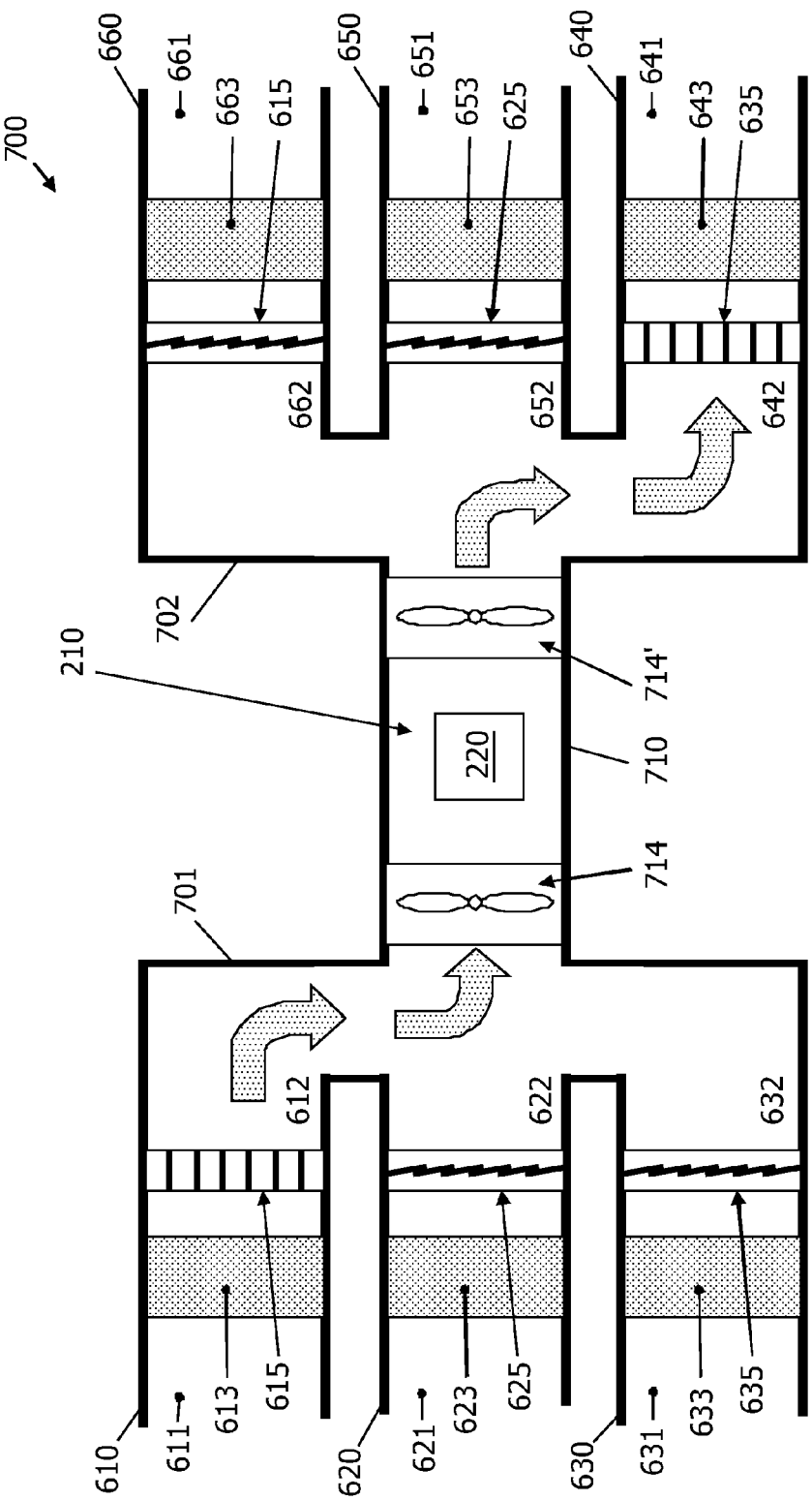

In the apparatus 600 as illustrated in FIG. 8, each duct is provided with an associated ventilator. Selecting the path which the gas flow takes in the apparatus, and thus selecting which filter is upstream of the sensor, is done by suitable control of the ventilators. However, alternative embodiments having the same functionality may have fewer ventilators. FIG. 9 illustrates an alternative apparatus 700 wherein each duct 610-660 is provided with a controllable closure device 615-665, for instance implemented as a shutter or a valve, controlled by the control device (not shown in this figure), such that the closure devices 625, 635, 655, 665 of the inactive ducts 620, 630, 650, 660 are always closed and the closure devices 615, 645 of the active ducts 610, 640 are always open. The apparatus 700 has a common duct 710 leading to/from the measuring chamber 210, and a ventilator 714 arranged in the common duct 710. In order to allow gas to flow in two opposite directions, the ventilator 714 may be a bi-directional ventilator, or it is possible to use a second ventilator 714', as shown.

Each duct in a pair of associated ducts is always coupled to one end or to the other end of the common duct 710, either via a first manifold 701 or a second manifold 702. With the ventilator 714 operating continuously, selecting the path which the gas flow takes in the apparatus, and thus selecting which filter 613 is upstream of the sensor 220, is done by suitable control of the closure devices.

An important advantage of the above embodiments is that the set-up is relatively simple and robust and, in view of the fact that only a single gas sensor is needed, they do not suffer from signal biasing problems.

The present invention also provides an apparatus with two (or more) sensors. An apparatus with two sensors involves the problem that it is difficult to ensure that the sensor responses of two different sensors positioned at two different locations are identical. However, such an apparatus offers the advantage that it is possible to provide a continuous result in real time, thereby enabling it to quickly note rapidly changing pollution conditions, and that it is actually possible to perform two measurements on the same air sample.

Figure 10:
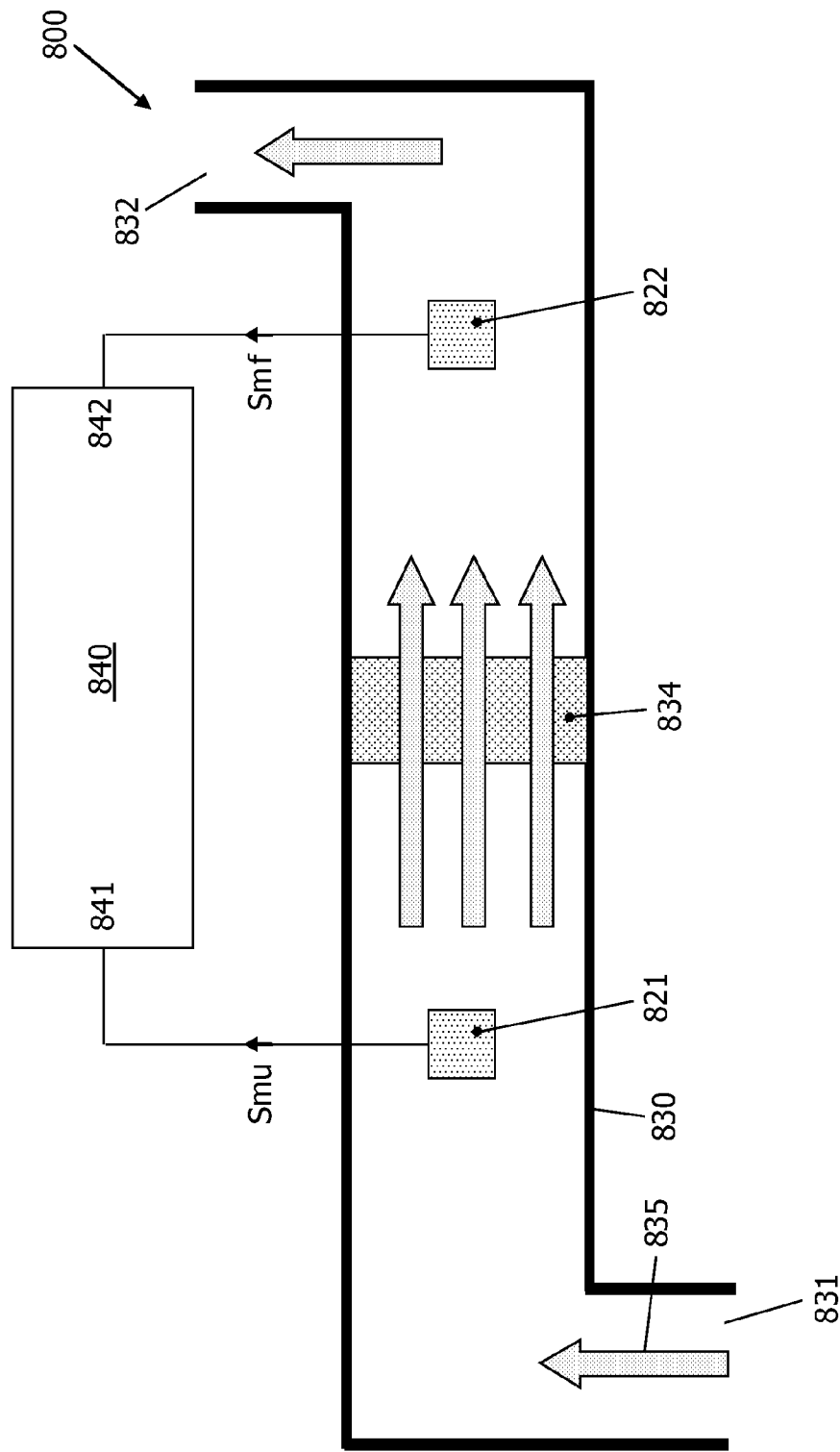
FIGS. 10-12 schematically illustrate several variations of embodiments of a gas sensing apparatus according to the present invention comprising at least two target gas sensors.

FIG. 10 illustrates an embodiment of a gas sensor apparatus 800 comprising an air duct 830 with an entrance 831 for allowing an airflow of ambient air 835 to enter the duct 830 and an exit 832 for allowing the airflow to be discharged. A target gas filter 834 is arranged in the air duct 830. A first sensor 821 is arranged upstream of the filter 834, between the entrance 831 and the filter 834, and a second sensor 822 is arranged downstream of the filter 834, between the filter 834 and the exit 832. The first sensor 821 is subjected to unfiltered air upstream of the filter 834; therefore its measuring signal is indicated as Smu. The second sensor 822 is subjected to filtered air downstream of the filter 834; therefore its measuring signal is indicated as Smf. A calculation device 840 has a first input 841 receiving the measuring output signal Smu from the first sensor 821 and a second input 842 receiving the measuring output signal Smf from the second sensor 822, and is thus capable of inferring the concentration of the target gas in the air from the signals Smu and Smf.

For driving the airflow 835, it is possible to arrange within the duct 830 an airflow generator such as for instance a ventilator, as in the case of the above-described embodiments, and such a generator may be arranged upstream or downstream of the filter 834. It is also possible to equip the apparatus with an external airflow generator, or any device capable of generating a pressure difference over the entrance 831 and output 832. It is even possible to have the apparatus cooperate with another apparatus, for instance a stand-alone air cleaner, which would include a ventilator to pass air through its cleaner units and hence causes a pressure difference.

Figure 11:
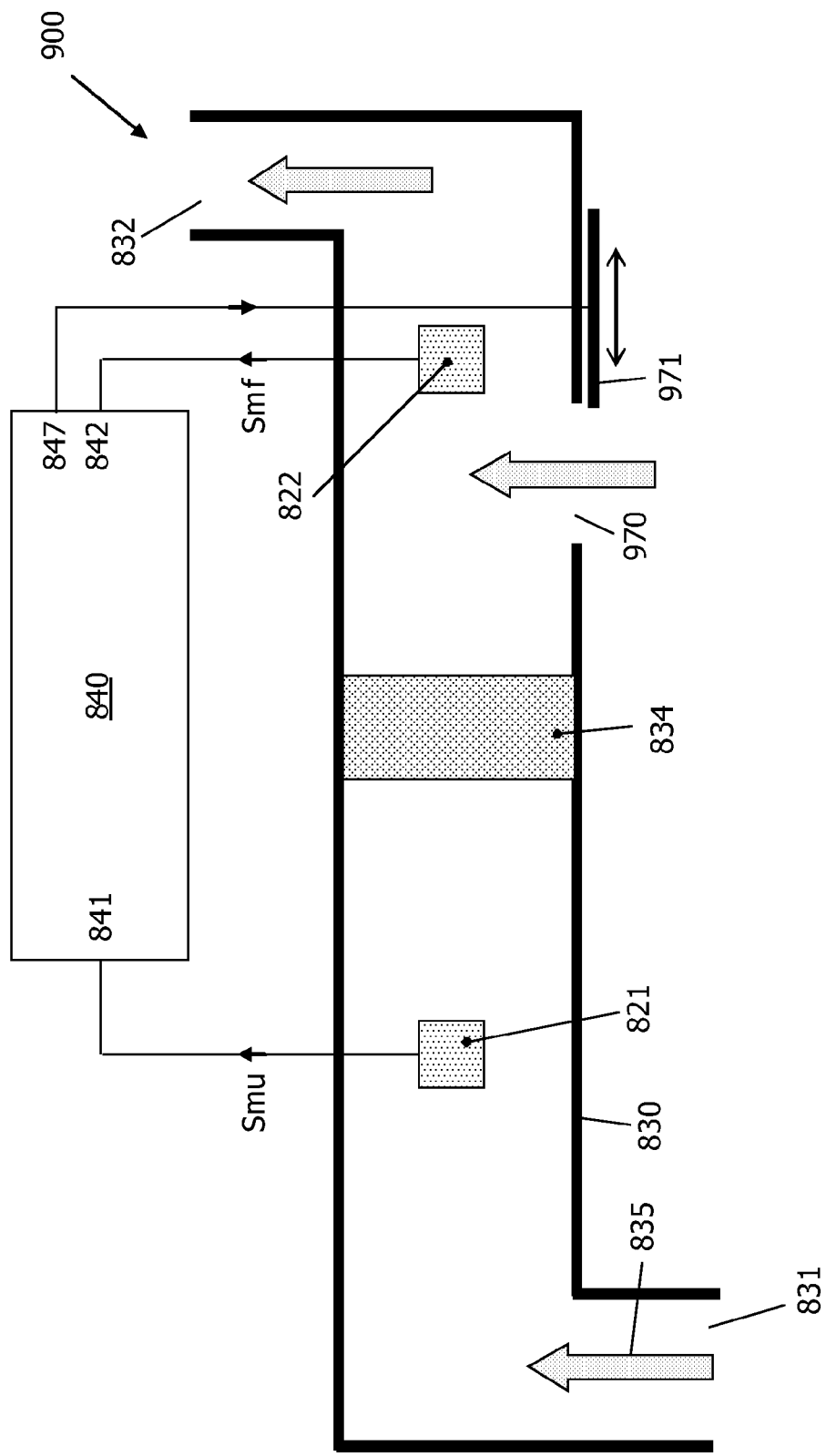

When the two sensors 821, 822 have identical characteristics, i.e. identical responses under otherwise identical conditions, their signals Smu and Smf can be directly compared, thus yielding a signal differential $S\Delta$=Smu−Smf that is directly proportional to the target gas concentration in the unfiltered ambient air. However, it may be that the two sensors 821, 822 exhibit a (perhaps slowly drifting) offset signal with respect to each other, or even if they don't, it may be desirable to be able to check this. FIG. 11 illustrates an embodiment of a gas sensing apparatus 900, which is a further elaboration of the apparatus 800 of FIG. 10. At a position downstream of the filter 834 and upstream of the second sensor 822, the duct 830 is provided with an opening 970 allowing the duct 830 to communicate with the ambient environment, which opening 970 is provided with a controllable valve or shutter or door 971, controlled by the unit 840 which now not only functions as a calculating device but also as control device. The figure illustrates the controllable shutter 971 as a moveable slide, but other implementations are also possible.

When the shutter 971 is closed, the apparatus 900 is in effect equivalent to the apparatus 800 of FIG. 10.

When the shutter 971 is in its "open" position, both sensors 821, 822 are exposed to unfiltered ambient air. It is noted that this applies even in the absence of an external pressure difference across the duct 830, or in the absence of an otherwise forced airflow, albeit that in such a case it may take somewhat longer for the unfiltered ambient air to reach the respective sensors. Preferably, the sensors 821, 822 are positioned close to the openings 831, 832, 970 to ensure quick and full exposure to unfiltered ambient air.

Due to the fact that sensors 821, 822 are now exposed to the same gas composition, and assuming that all other parameters at the two different sensing locations are mutually identical or do not have any significant influence on the sensor output signals, the two sensor output signals should ideally be mutually identical, and any difference $\Delta$ between these signals represents an offset. Without the cause of such offset being known, it is possible for the calculating portion of the unit 840 to compensate for the offset.

Thus, the apparatus 900 is capable of operating in a measuring mode and in a calibration mode, and the control device 840 is designed to regularly switch to the calibration mode. In the calibration mode, the control device 840 opens the shutter 971 and calculates the difference $\Delta$ between the two measuring signals Smu and Smf received from the two sensors 821, 822, according to $\Delta$=Smu−Smf. In the measuring mode, the control device 840 closes the shutter 971 and calculates a compensated measuring output signal S$\Delta$c of the apparatus 900 according to the formula $$S\Delta c = Smu - Smf - \Delta$$

which represents the concentration of the target gas in the unfiltered ambient air.

Figure 12:
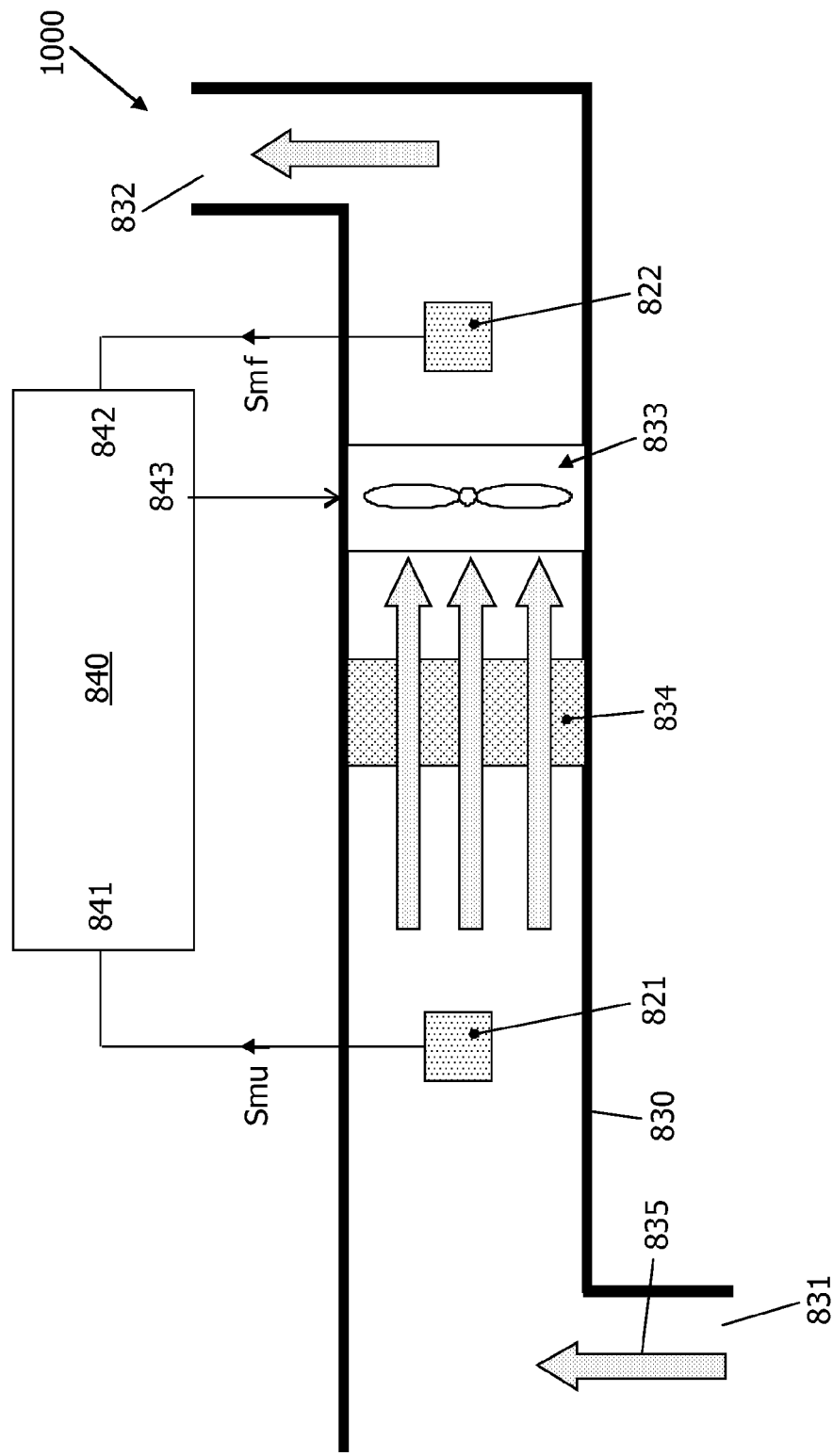

FIG. 12 illustrates an apparatus 1000 which is a further elaboration of the apparatus 800 of FIG. 10, comprising a controllable bi-directional ventilator 833 arranged in the duct 830, and controlled by the control device 840 at an output 843 thereof. With the ventilator operating as shown, the operation is equivalent to that of the apparatus 800 of FIG. 10: the first sensor 821 is upstream of the filter 834 and provides an unfiltered measuring signal while the second sensor 822 is downstream of the filter 834 and provides a filtered measuring signal. When the control device 840 operates the ventilator 833 in the opposite direction, the second sensor 822 is upstream of the filter 834 and provides an unfiltered measuring signal while the first sensor 821 is downstream of the filter 834 and provides a filtered measuring signal. Any offset between the two sensors can now be determined by comparing the two unfiltered measuring signals from the two sensors and/or by comparing the two filtered measuring signals from the two sensors.

It is noted that the principles of the invention as described above do not depend on the type of gas sensor. Basically, any known gas sensor can be used, or even future gas sensors will be useable. All embodiments as described are capable of automated operation without being dependent on human intervention.

Further, it is noted that the principles of the invention as described above do not depend on the type of target gas filter. However, it is preferred to use a filter type that combines high filter efficiency with low flow resistance and long filter lifetime. By way of example, the target gas filter structure may be a corrugated structure, a parallel-plate structure or a granular filter bed. Such filters are disclosed in U.S. Pat. No. 6,071,479 and allow for a much higher target gas filtration capacity than the sheet filters used by Environmental Sensors mentioned in the introduction. The corrugated structure and parallel-plate structure are preferably made from a fibrous hydrophilic paper material or from a hydrophilic glass-fiber material, which can readily be filled with an aqueous solution of the desired reagent species. After drying, the impregnated reactant species inside the filter remain hydrated in equilibrium with the ambient humidity and can subsequently absorb a target gas from the air. The granular filter is preferably composed from activated carbon, zeolites, activated alumina or any other porous granular material. These materials can also be readily impregnated. Impregnation of these porous materials leaves the width of the air passage channels inside the filter essentially unchanged. Thus, impregnation does not change the diffusive barrier properties of the filter structure with respect to (?) gaseous species. The height of these filters can be readily adjusted, thereby changing the amount of impregnant that can be comprised inside these filters and thus their effective lifetime. Various examples of impregnant compositions that are effective absorbers of (?) formaldehyde, acidic gases or alkaline gases are disclosed in U.S. Pat. No. 6,071,479.

As an example, in the case that the target gas is formaldehyde, an advantageous aqueous impregnant solution comprises $KHCO_3$ (2-20% w/w), $K_2CO_3$ (1-20% w/w), Trishydroxymethyl-aminomethane (3-30% w/w), Kformate (2-20% w/w).

A more preferred impregnant solution comprises:
$KHCO_3$ (10% w/w)
$K_2CO_3$ (5% w/w)
Trishydroxymethyl-aminomethane (5-25% w/w)
Kformate (5-10% w/w)

The $KHCO_3$ and $K_2CO_3$ species are examples of alkaline impregnants that are capable of absorbing acidic gases such as $HNO_x$, $SO_2$ and organic carboxylic acids from air. Trishydroxymethyl-aminomethane is the impregnant capable of absorbing formaldehyde from air. Thus, the filter comprising the more preferred impregnant solution mentioned above is capable of absorbing the class of gases comprising $HNO_x$, $SO_2$ and organic carboxylic acids and the target gas formaldehyde. In the case that Tris-hydroxymethyl-aminomethane is omitted from the preferred impregnant solution, the filter is only capable of absorbing the class of gases comprising $HNO_x$, $SO_2$ and organic carboxylic acids.

While the invention has been illustrated and described in detail in the drawings and foregoing description, it should be clear to a person skilled in the art that such illustration and description are to be considered illustrative or exemplary and not restrictive. The invention is not limited to the disclosed embodiments; rather, several variations and modifications are possible within the protective scope of the invention as defined in the appending claims. It is noted that, in daily practice, the phrase "ambient air" may relate to the mixture of nitrogen and oxygen that we breathe, but in the context of the present invention, the sensing apparatus is basically applicable in any type of gas atmosphere and the phrase "ambient gas" is used to indicate the gas atmosphere in which the apparatus is placed.

It is further noted that an apparatus according to the present invention with one gas sensor exposes the gas sensor to two different gas flows during two different time intervals, but the order of these two intervals is not essential.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

In the above, the present invention has been explained with reference to block diagrams, which illustrate functional blocks of the device according to the present invention. It is to be understood that one or more of these functional blocks may be implemented in hardware, where the function of such (a) functional block(s) is performed by individual hardware components, but it is also possible that one or more of these functional blocks are implemented in software, so that the function of such (a) functional block(s) is performed by one or more program lines of a computer program or a programmable device such as a microprocessor, microcontroller, digital signal processor, etc.

The invention claimed is:

1. Method of determining the concentration of a target gas in ambient air, the method comprising the steps of:
   providing a target gas sensor that is sensitive to at least the target gas;
   providing a first gas flow derived from the ambient air, the target gas being substantially removed from the first gas flow;
   providing a second gas flow derived from the ambient air, substantially without removing the target gas;
   exposing the target gas sensor to the first gas flow, and obtaining from the target gas sensor a first sensor signal (Smf);
   exposing the target gas sensor to the second gas flow, and obtaining from the target gas sensor a second sensor signal (Smu);
   determining the concentration of the target gas from the first sensor signal and the second sensor signal.

2. Method according to claim 1, wherein the second gas flow is unfiltered ambient air.

3. Method according to claim 1, wherein at least one specific gas, or group of gases, or class of gases, not including the target gas, is substantially removed from both the first gas flow and the second gas flow.

4. Method according to claim 1, wherein the first gas flow is generated by operating a controllable flow generator, and wherein the second gas flow is generated by switching off the controllable flow generator.

5. Method according to claim 1, wherein the first gas flow is generated by operating a controllable flow generator in a first direction, and wherein the second gas flow is generated by operating the controllable flow generator in the opposite direction.

6. Gas sensing apparatus for determining the concentration of a target gas in ambient air, the apparatus comprising:
   at least one target gas sensor and a target gas filter;
   at least one controllable gas flow generating means for generating a gas flow derived from the ambient air;
   a control device for controlling the gas flow generating means and receiving measuring output signals from the target gas sensor;
   the apparatus being able to selectively operate in at least two different operational modes;
   wherein the control device is designed, in a first operational mode, to control the gas flow generating means to generate a first gas flow through the target gas filter to the target gas sensor, with the target gas sensor being downstream with respect to the target gas filter;
   wherein the control device is designed, in a second operational mode, to allow a second gas flow to reach the target gas sensor, the second gas flow comprising the target gas in the same concentration as in the ambient air;
   wherein the control device is designed to receive a first sensor output signal Smf from the target gas sensor in the first operational mode, and to receive a second sensor output signal Smu from the target gas sensor in the second operational mode, wherein the control device (240) is designed to determine the concentration of the target gas in the ambient air from the first sensor output signal Smf and the second sensor output signal Smu.

7. Apparatus according to claim 6, wherein the control device is designed, in the second operational mode, to switch off the gas flow generating means to allow unfiltered ambient air to reach the target gas sensor convectively.

8. Apparatus according to claim 6, wherein the control device is designed, in the second operational mode, to operate the gas flow generating means to generate a second gas flow in a direction opposite to the first gas flow direction.

9. Apparatus according to claim 6, further comprising a second gas flow generating means, wherein the control device is designed, in the second operational mode, to operate the second gas flow generating means to generate a second gas flow in a direction opposite to the first gas flow direction.

10. Gas sensing apparatus according to claim 6, further comprising a second gas filter, wherein the second gas filter is designed to remove from ambient air at least one specific gas or group of gases or class of gases, wherein the first target gas filter is designed to remove from ambient air the same gases as the second gas filter and also the target gas, and wherein in the first operational mode the sensor is downstream of the first target gas filter while in the second operational mode the sensor is downstream of the second gas filter.

11. Gas sensing apparatus according to claim 10, further comprising a second set of target gas filter and second gas filter on opposite sides of the sensor, and further comprising controllable flow selection means for causing a gas flow to the sensor either via the first target gas filter or the corresponding second filter or via the second target gas filter or the corresponding second filter.

12. Gas sensing apparatus according to claim 6, wherein the control device) is designed to regularly alternate between the first operational mode and the second operational mode.

13. Gas sensing apparatus according to claim 6, wherein the target gas filter comprises a carrier structure having air passage channels, the carrier material being impregnated with an impregnant composition effective to absorb the target pollution component, and wherein, if the target pollution component is formaldehyde, the impregnant composition preferably comprises $KHCO_3$, $K_2CO_3$, Trishydroxy-methyl-aminomethane, and Kformate.

14. Gas sensing apparatus for determining the concentration of a target gas in ambient air, the apparatus comprising:
- a series arrangement of a target gas filter and two gas sensors on opposite sides of the target gas filter, wherein a first gas sensor is arranged upstream of the target gas filter for providing a measuring output signal (Smu) relating to unfiltered ambient gas and a second gas sensor is arranged downstream of the target gas filter for providing a measuring output signal (Smf) relating to filtered ambient gas;
- a calculating device receiving the measuring output signals from the gas sensors;
- wherein the calculating device is designed to calculate a difference signal (SΔ=Smu−Smf) between the said two measuring output signals and to derive from said difference signal the concentration of the target gas in the ambient air.

15. Gas sensing apparatus according to claim 14, further provided with an opening at a position downstream of the target gas filter and upstream of the second sensor, the opening being provided with a controllable closure device;
- the apparatus comprising a control device for controlling the closure device;
- wherein the apparatus is capable of operating in a calibration mode, in which the control device is designed to open the closure device and calculate a difference (Δ) between the two measuring signals (Smu, Smf) received from the two sensors, representing an offset between said two sensors;
- and wherein the apparatus is capable of operating in a measuring mode, in which the control device is designed to close the closure device and calculate a compensated measuring output signal (SΔc) of the apparatus, representing the concentration of pollutant in the gas, according to the formula $$S\Delta c = Smu - Smf - \Delta$$

in which:
SΔc indicates the compensated measuring output signal;
Smu indicates the measuring output signal of the first gas sensor;
Smf indicates the measuring output signal of the second gas sensor;
Δ indicates the said difference calculated in the calibration mode.

* * * * *